United States Patent
Rehkopf et al.

(10) Patent No.: US 9,809,619 B2
(45) Date of Patent: Nov. 7, 2017

(54) PULSE COMBUSTION DRYING OF PROTEINS

(71) Applicant: Pulse Holdings, LLC, Payson, AZ (US)

(72) Inventors: James A. Rehkopf, San Rafael, CA (US); David A. Mirko, Payson, AZ (US)

(73) Assignee: PULSE HOLDINGS, LLC, Payson, AZ (US)

( * ) Notice: Subject to any disclaimer, the term of this patent is extended or adjusted under 35 U.S.C. 154(b) by 301 days.

(21) Appl. No.: 14/596,996

(22) Filed: Jan. 14, 2015

(65) Prior Publication Data

US 2015/0197541 A1    Jul. 16, 2015

Related U.S. Application Data

(60) Provisional application No. 61/927,068, filed on Jan. 14, 2014.

(51) Int. Cl.
*C07K 1/14* (2006.01)
*C07K 14/78* (2006.01)
*C07K 14/415* (2006.01)

(52) U.S. Cl.
CPC .............. *C07K 1/14* (2013.01); *C07K 14/415* (2013.01); *C07K 14/78* (2013.01); *Y10T 428/2982* (2015.01)

(58) Field of Classification Search
CPC ........ C07K 1/14; C07K 14/78; C07K 14/415; Y10T 428/2982
See application file for complete search history.

(56) References Cited

U.S. PATENT DOCUMENTS

| | | | | | |
|---|---|---|---|---|---|
| 2,087,985 | A | * | 7/1937 | McCharles | A23B 5/025 426/330.1 |
| 2,299,953 | A | * | 10/1942 | Mink | A23B 5/022 159/DIG. 4 |
| 2,571,459 | A | * | 10/1951 | Lindsay | A23B 5/022 159/4.07 |
| 2,921,857 | A | * | 1/1960 | Sharp | A23C 1/05 159/48.1 |
| 4,475,295 | A | * | 10/1984 | Hussmann | A23F 5/285 34/213 |
| 5,252,061 | A | * | 10/1993 | Ozer | F23C 15/00 34/365 |

(Continued)

FOREIGN PATENT DOCUMENTS

CN    101806534    *    8/2010

OTHER PUBLICATIONS

Zbicinski et al. Brazillian Journal of Chemical Engineering. vol. 17. No. 4-7. Dec. 2000. pp. 1-7.*

(Continued)

*Primary Examiner* — Anthony Weier
(74) *Attorney, Agent, or Firm* — Benjamin C. Armitage; Billion & Armitage

(57) ABSTRACT

Methods for pulse combustion spray drying of heat-sensitive protein compositions using high temperature pulsating jets to atomize and dry the feed simultaneously are described herein. Methods and compositions described herein provide dried protein-containing compositions with low protein denaturation and other useful functional properties at high operational efficiencies.

13 Claims, 9 Drawing Sheets

(56) References Cited

U.S. PATENT DOCUMENTS

Figure 1A:
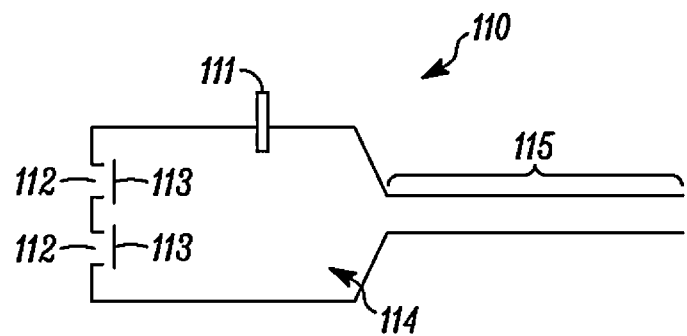
Figure 1B:
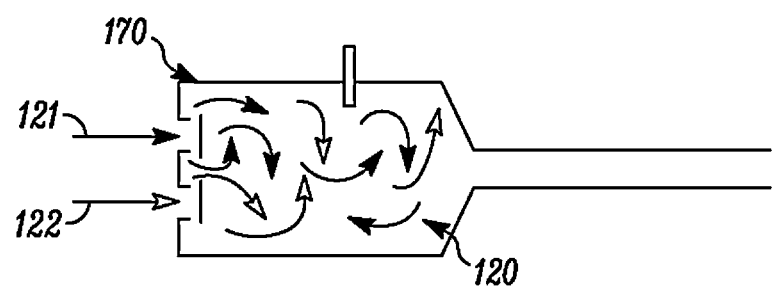
Figure 1C:
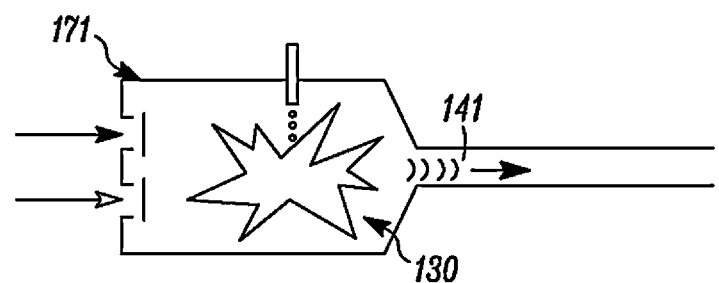
Figure 1D:
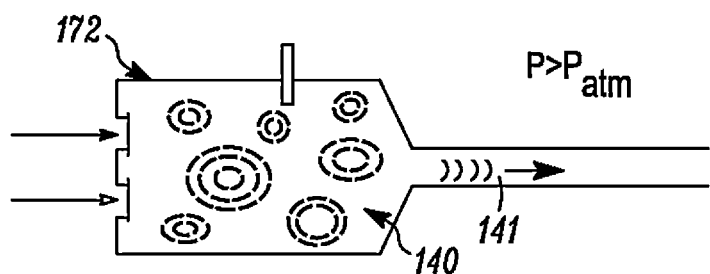
Figure 1E:
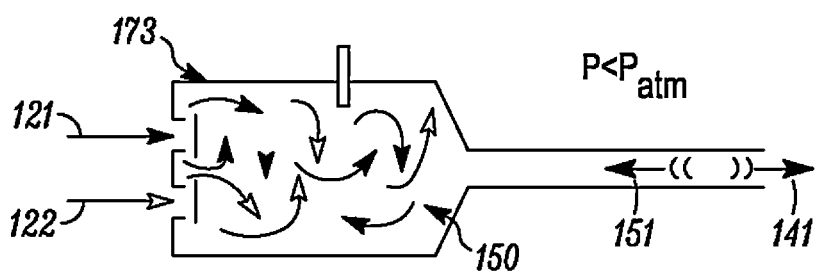
Figure 1F:
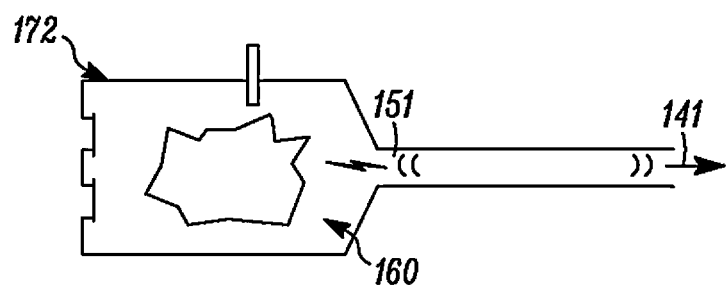
Figure 2:
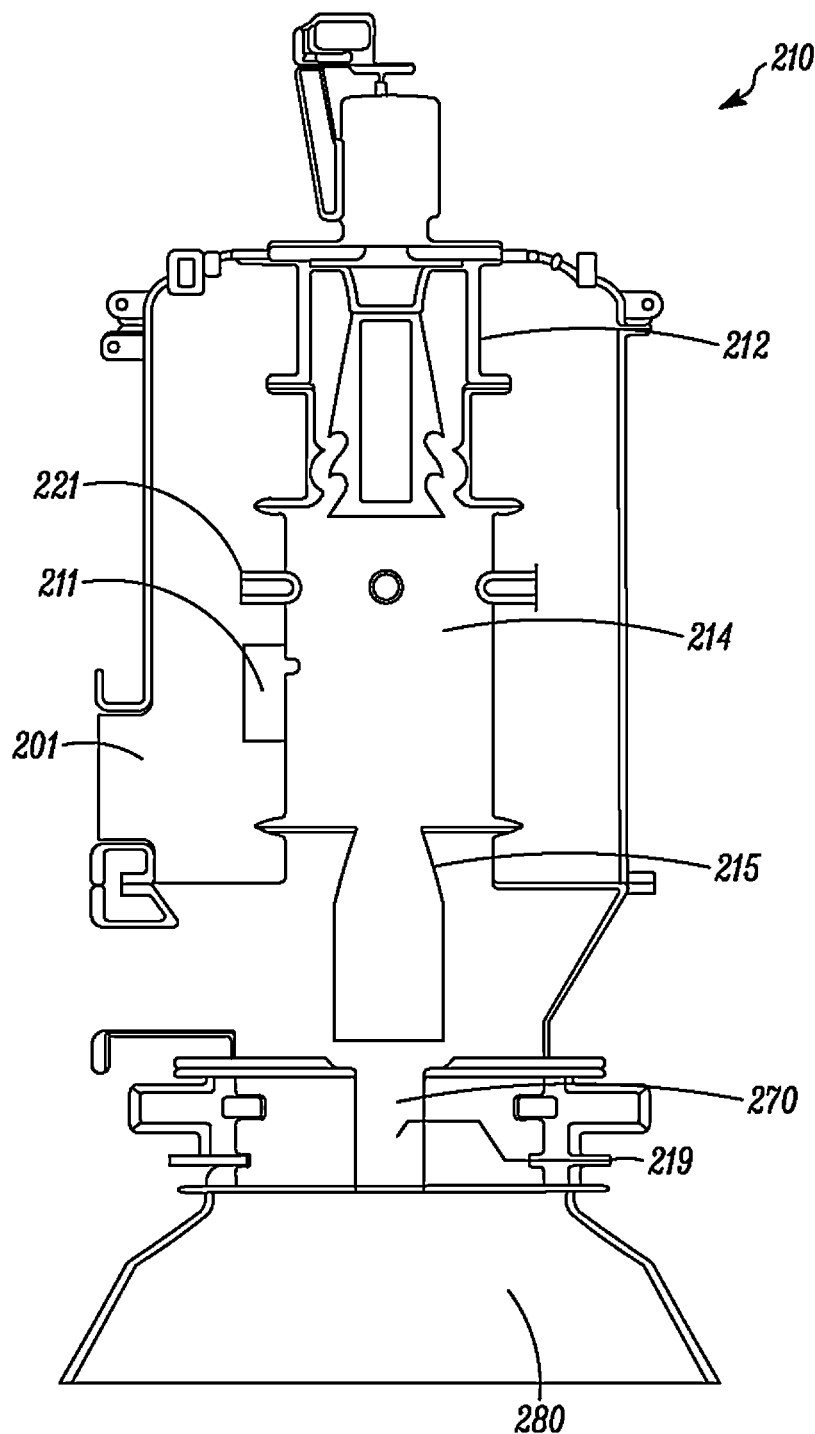

| | | | | |
|---|---|---|---|---|
| 5,638,609 | A | * | 6/1997 | Chandran ............... F23C 15/00 34/365 |
| 7,322,124 | B2 | * | 1/2008 | Bouman ................. B01D 1/18 34/138 |
| 9,139,627 | B2 | * | 9/2015 | Riebel ...................... C08H 1/00 |
| 2008/0226805 | A1 | * | 9/2008 | Watanabe ............... A23L 15/35 426/614 |
| 2009/0269477 | A1 | * | 10/2009 | Tate ......................... C12F 3/10 426/656 |
| 2009/0281203 | A1 | * | 11/2009 | Riebel ...................... C12F 3/10 521/44 |

OTHER PUBLICATIONS

Mujumdar. Handbook of Industrial Drying. 4th Edition. Jul. 2014. pp. 509-511.*
English Translation for CN101806534 published Aug. 2010.*
Spreer. Milk and Dairy Product Technology. 1998. p. 389.*
Wu, Z., et al. Food Bioprocess Technol (2015) 8: 148. doi:10.1007/s11947-014-1384-9.

* cited by examiner

PULSE COMBUSTION DRYING OF PROTEINS

BACKGROUND

Heat-sensitive protein compositions (HSPC) are widely applicable in food and nutraceutical industries. For example, egg white is qualified as a multi-purpose ingredient due to its high nutritional qualities and excellent foaming and gelling properties. Many HSPCs are commercialized under liquid solution forms but dried particulate forms can be preferable as they offer longer shelf lives and enhanced ease of transport, storage, and use. In drying HSPCs, energy efficiency and product quality are the primary concerns yet achieving one concern often frustrates the purpose of the other. High-temperature drying processes can achieve the highest drying efficiencies, but can have a detrimental effect on the functional properties of heat-sensitive proteins. For example, liquid egg whites comprise about 80% to 95% water, and the energy imparted to evaporate the water can induce protein denaturation which reduces functional properties of the egg white such as foaming and gelling properties. Similarly, high temperature drying of milk can degrade bio-activity of constituent enzymes and overall product taste.

Many HSPCs are traditionally dried by spray drying methods, which include spraying an HSPC feed via rotary atomizers or nozzles into a hot drying medium to remove moisture and provide a dried particulate form. In order to operate efficiently, spray drying must be conducted at HSPC-damaging temperatures, for example temperatures above a denaturation temperature of one or more proteins. Most spray dryers operate at temperature below denaturation temperatures, but process efficiency suffers as a result. Further, spray dryer rotary atomizers and nozzles clog easily when conveying higher viscosity or particulate-containing feeds. Spray dryers also suffer from technical difficulties, particularly due to wear on rotary atomizers and nozzles which over time reduce feed flow rate conveying accuracy and increase maintenance costs and unit down-time.

SUMMARY

In general, this disclosure describes techniques for drying heat sensitive protein compositions (HSPD) using high temperature pulsed air streams. In some Embodiments, the technique includes using pulsating jets to atomize and dry the feed simultaneously. The techniques described herein provide high energy efficiency per unit water evaporated, and provides low-moisture compositions having superior physical and functional properties.

In some embodiments, a method for producing a dried protein-containing composition can include introducing a heat-sensitive protein composition into a drying chamber, wherein the heat-sensitive protein composition comprises water and one or more proteins; drying the heat-sensitive protein composition by contacting the heat-sensitive protein composition with a pulsed gas stream of a pulse combustion dryer; controlling the drying chamber outlet temperature such that it does not substantially exceed a denaturation temperature of one or more proteins in the heat-sensitive protein composition; and recovering a dried protein-containing composition.

In some embodiments, a dried, heat-sensitive protein composition can comprise solid particles including one or more proteins forming a protein fraction, wherein less than about 10% of the protein fraction includes denatured proteins. In some other embodiments the dried, heat-sensitive protein composition can further comprise a total water content of less than 10% by weight.

Some embodiments comprise a dried, heat-sensitive protein composition prepared by a process comprising the steps of: introducing a heat-sensitive protein composition into a drying chamber, wherein the heat-sensitive protein composition comprises water and one or more proteins; drying the heat-sensitive protein composition by contacting the heat-sensitive protein composition with a pulsed gas stream of a pulse combustion dryer; controlling the drying chamber outlet temperature such that it does not substantially exceed a denaturation temperature of one or more proteins in the heat-sensitive protein composition; and recovering a dried protein-containing composition.

Techniques described herein provide dried egg whites with superior physical characteristics and properties as compared to egg whites dried by other traditional drying methods such as spray drying.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 1A, 1B, 1C, 1D, 1E, and 1F illustrate the operation of a Hemholtz-type pulse combustor with flapper valves, according to an embodiment of this disclosure.

FIG. 2 illustrates a schematic view of a pulse combustor and atomizer, according to an embodiment of this disclosure.

FIG. 3A illustrates a schematic of a pulse combustion spray drying system, according to one or more techniques of this disclosure.

FIGS. 3B and 3C illustrate flow diagrams for pulse combustion drying methods of heat-sensitive protein compositions, according to one or more embodiments of this disclosure.

FIG. 4A illustrates egg white powders dried using pulse combustion spray dryers, according to an embodiment of this disclosure.

FIG. 4B illustrates egg Kangde™ white powders dried using traditional spray drying, according to an embodiment of this disclosure.

FIG. 5 illustrates a graph of the size distributions of pulse combustion spray dried egg whites and Kangde™ SD egg white powders, according to an embodiment of this disclosure.

FIG. 6A illustrates an SEM image of pulse combustion spray dried egg white powders, according to an embodiment of this disclosure.

FIG. 6B illustrates an SEM image of Kangde™ egg white powders dried using traditional spray drying techniques, according to an embodiment of this disclosure.

FIG. 7 illustrates a graph of the differential scanning calorimetry curves for the pulse combustion spray dried powders and the LHAD sample powders, according to an embodiment of this disclosure.

FIG. 8 illustrates a graph of differential scanning calorimetry curves for various egg white drying methods, according to an embodiment of this disclosure.

DETAILED DESCRIPTION

The energy efficiency and product quality contradiction described above may be solved by a novel spray drying technique-pulse combustion spray drying (PCSD). Unlike traditional spray drying where liquid atomization and drying are separated, the PCSD technique uses pulse combustion technology to produce high temperature and high velocity pulsating jets, which are used to atomize and dry the liquid simultaneously. Since PCSD dryers use "gas dynamic" atomization and no mechanical atomizers/nozzles are needed, they can handle liquids with high viscosity and/or high solid content which are normally problematic for traditional spray drying. More importantly, PCSD dryers can provide an advantageous superposition of unsteady gas flow and high-intensity sound waves. Such a combination increases the momentum and heat/mass transfer rates in industrial drying processes and thus improves the dryers' energy efficiency. PCSD dyers have other merits including low pressure in the liquid feed system, lower maintenance costs, and enhanced operational control.

Examples of PCSD apparatus and methods are described in co-owned U.S. Pat. Nos. 8,517,723 B2, 7,937,850 B2, 8,697,156 B2, 8,037,620 B2, and 8,490,292 B2, and U.S. Application Publication No. 2012/0291396 A1, which are herein incorporated in their entirety.

As described herein, PCSD techniques have numerous novel applications for drying of food and nutraceutical materials, particularly heat-sensitive protein compositions (HSPC). HSPCs can comprise one or more proteins. In some embodiments, HSPCs can further comprise water. In other embodiments, HSPCs can further comprise additional components such as fats and carbohydrates. Additional components are often common components of a HSPC. For example, an HSPC such as egg white can contain numerous proteins, water, fats, and carbohydrates.

Heat-sensitive protein compositions (HSPC) are compositions comprising a protein fraction susceptible to degradation by heat. An example HSPC is egg white, which can include about 80% to about 95% water and a dry matter fraction comprising over about 80% heat-sensitive proteins. Egg white powders are a desirable ingredient for many foods such as bakery products, meringues and meat products, as they have excellent foaming and gelling properties. Additionally or alternatively HSPCs can include gelatins, casein, milk proteins, soy proteins, whey proteins, gluten, or any other composition including proteins susceptible to degradation by heat. Degradation can include a diminishment of useful properties, such as physical or functional properties.

Physical and/or functional properties can include protein denaturation, protein oxidation, enzymatic activity, foaming ability, foam stability, gel hardness, gel springiness, particle morphology, particle size, and color. An application of heat to a protein can cause denaturation, or an alteration of a protein's native structure. For example, and alteration can include a protein losing its native quaternary, tertiary, or secondary structure. Such an alteration can result in communal aggregation, loss of solubility, and a change of functional properties such as foaming and gelling abilities, and bioactivity. In general, the denaturation temperature of proteins is about 75~90° C., making proteins very susceptible to denaturation in high temperature drying processes such as traditional spray drying. For example, up to 70% whey protein isolate can be denatured during spray drying. The denaturation temperature for a HSPC can include the denaturation temperature of the most prevalent protein, a weighted average of the denaturation temperature of the one or more protein components, or an average of the denaturation temperature of the one or more protein components. The denaturation temperature for a HSPC can also be the temperature at which an appreciable denaturation effect is observed on the proteins of an HSPC.

Pulse combustion originates from the intermittent (pulse) combustion the solid, liquid, or gaseous fuel in contrast to the continuous combustion in conventional burner. Such periodic combustion generates intensive pressure, velocity, and, to a certain extent, temperature waves propagated from the combustion chamber via a tailpipe to the process volume (applicator) such as a drying chamber. Due to the oscillatory nature of the momentum transfer, pulse combustion intensifies the rates of heat and mass transfer and accelerates drying rates.

FIGS. 1A-F show the operating stages of a Helmholtz-type pulse combustor 110 with flapper valves 113, which in some embodiments comprises a component of a PSCD system. Those of skill in the art will recognize that combustors capable of providing the operating conditions described herein to be similarly suitable. The controlling mechanism behind the operation of a pulse combustor is a complex interaction between an oscillatory combustion process and acoustic waves that are propagated from the combustor. The major function of the pulse combustor in a drying system is to supply heat for moisture evaporation and to generate large-amplitude, high frequency pressure pulsations within a drying chamber, which can each separately or in combination enhance drying rates. The strong oscillating hot flue gas jet generated by the pulse combustor can also promote dispersion of the feed.

As shown in FIGS. 1A-F, pulse combustion starts when fuel 121 and combustion air 122 are drawn into the combustion chamber 114 and mixed to form a mixture 120. The mixture 120 is ignited 130 by an ignitor 111, such as a spark plug, and combusts 140 the mixture 120 explosively, resulting in a rapid pressure rise. At this moment, the rising pressure closes 171 the valves 113, sealing the air and fuel inlet ports 112 and forcing the combustion products 141 to flow out through the tailpipe 115. As the hot flue gases 141 flow out, the resulting outward momentum causes the pressure in the combustion chamber 114 to drop to the minimum so the valves 113 open, which admits fresh fuel 121 and air 122 into the combustion chamber 114. This new charge ignites itself 160 due to contact with remnants of hot flue gases 151 left in the tailpipe from the preceding cycle which reenter the combustion 114 chamber during the minimum pressure period 150. These combustion cycles repeat at a natural frequency depending on the geometry of the combustion chamber and characteristics of the tailpipe-applicator system. The expelled combustion products 141 are directed into a drying chamber (not pictured) where they contact a drying substrate, such as a HSPC.

FIG. 2 shows how a pulse combustor can be used to atomize and/or dry a liquid feed. In this and other embodiments, the term “liquid” can refer to liquids, fluids, fluidized powders, slurries, suspensions, dispersions, emulsions, and the like. Air 201 is pumped into the pulse combustor 210 outer shell at a low pressure where it flows through the unidirectional air valve 212; the air enters a tuned combustion chamber 214 where fuel 221 is added; the air valve 212 closes; the fuel-air mixture is ignited by a pilot 211 and combusts or explodes creating hot air which can be pressurized to, for example, about 2 kPa above the combustion fan pressure; the hot gases rush down the tailpipe 215 toward the atomizer 270; the air valve 212 reopens and allows the next air charge to enter; the fuel valve admits fuel 221; and the mixture explodes in the hot chamber. This cycle is controllable from about 50 Hz to about 200 Hz, or in some embodiments from about 80 Hz to 110 Hz. Just above the atomizer 270, quench air is blended in to achieve desired product contact temperature; the exclusive PCS atomizer releases the liquid feed 219 into a carefully balanced gas flow, which dynamically controls atomization, drying, and particle trajectory; the atomized liquid enters a conventional tall-form drying chamber 280; downstream, the suspended powder is retrieved using any commercially acceptable means, such as a cyclone and/or bag house.

Typically, a pulse combustor may operate at frequencies that vary from 20 to 200 Hz. Pressure oscillations in the combustion chamber of the order of ±10 kPa produce velocity oscillations of about ±100 meters per second and the velocity of the gas jet exiting the tailpipe varies from about 0 meters per second to about 200 meters per second. The input power ranges from about 20 kW to about 1000 kW for commercially available pulse combustors, although other input power ranges are practicable.

Figure 3A:
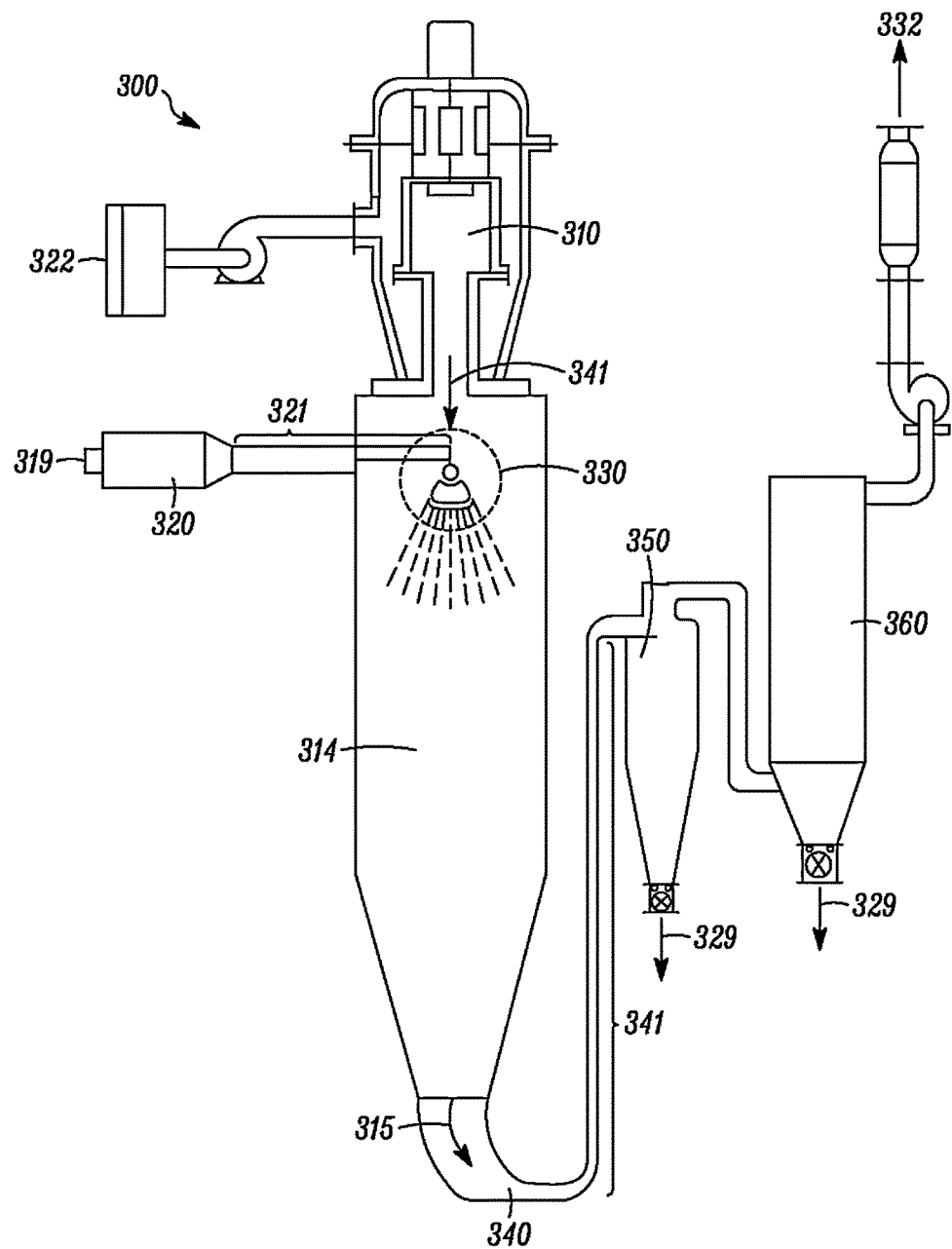

FIG. 3A shows an example of a pulse combustion spray drying system 300 which can be used for the techniques described herein. The system 300 comprises, among other things, a pulse combustion burner 310 and air supply 322 in fluid communication with drying chamber 314. Feed 319 is directed into the drying chamber 314 via a feed conveyer 320. The feed conveyer 320 can comprise a low-pressure, open pipe feed system, which provides the ability to process feeds having higher solids contents. This obviates the need to dilute the feed material in order to atomize it, yielding higher powder production rates and much lower processing costs per finished pound. Feed 319 contacts the pulse combustor combustion air 341 in zone 330. Zone 330 can in some embodiments be referred to as the high heat zone, wherein feed 319 is exposed to peak combustion air 341 temperatures. After the feed 319 contacts the combustion air 341, it travels out of the drying chamber 314 via a pipe or duct 340. A section of piping after the drying chamber 314, for example, piping section 341 can be cooled, to maintain the dried product 315 at a desired temperature. Similarly, a piping section 321 can be cooled such that feed 319 is not prematurely exposed to heat, or elevated above a desired initial temperature. Dried feed 315 can be processed in one or more of a cyclone 350 and bag house 360, each of which can yield final product 329. Exhaust air 332 can be expelled at the end of the system line.

Figure 3C:
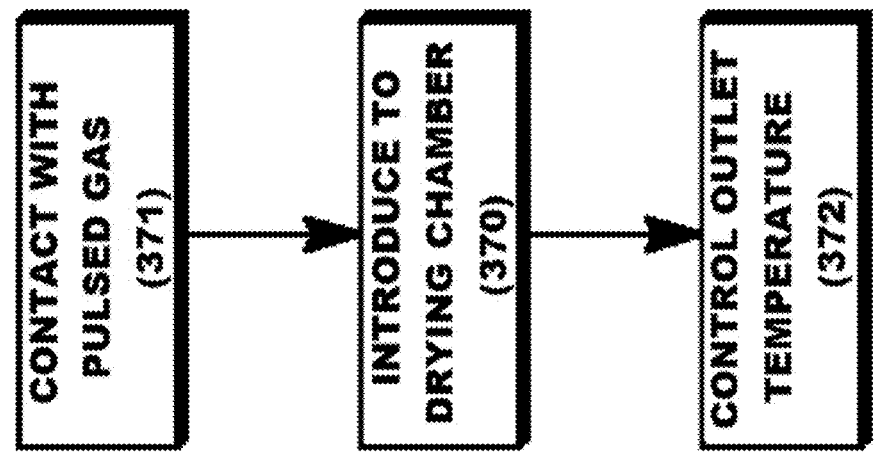

As shown in FIG. 3C, methods for producing a dried protein-containing composition can comprise drying a HSPC by contacting 371 the HSPC with a pulsed gas stream of a pulse combustion dryer. In some embodiments, methods further comprise introducing 370 a HSPC into a drying chamber. In other embodiments, methods can further comprise controlling 372 the drying chamber outlet temperature such that it does not substantially exceed a denaturation temperature of one or more proteins in the heat-sensitive protein composition. In some other embodiments, methods further comprise recovering a dried protein-containing composition Energy-efficient PCSD drying methods can effectively yield dried HSPC with low denaturation levels, even while utilizing drying gas having initial contact temperatures exceeding denaturation temperatures of proteins by 50° C., by 100° C., by 150° C., by 200° C., by 250° C., or by equal to or over 350° C. This is due to a number of factors, including short residence time of HSPCs within one or more of the high heat zone and within the PCSD drying chamber, and high oscillation of HSPCs within a drying chamber. Under such conditions, an HSPC is dried without raising the HSPC temperature above its protein denaturation temperature. Drying an HSPC without raising the HSPC temperature above its protein denaturation temperature can be achieved in some embodiments by manipulating one or more of the pulsed gas stream temperature, a residence time of the heat-sensitive protein composition within the drying chamber, pulsed gas stream pulse frequency, pulsed gas stream exit temperature, or feed flow rate. In some embodiments, an HSPC can be dried using PCSD wherein the HSPC is heated above a denaturation temperature. However, due to the extremely short residence times, the HSPC experiences only minimal denaturation.

Residence times can include less than about 10 seconds, less than about 9 seconds, less than about 8 seconds, less than about 7 seconds, less than about 6 seconds, less than about 5 seconds, less than about 4 seconds, less than about 3 seconds, less than about 2 seconds, less than about 1 second, or less than about 0.5 seconds. Residence time describes the time that a given feed particle spends in a drying chamber. In many embodiments, a PCSD drying chamber has a high heat zone in which a HSPC is only exposed to a maximum drying gas temperature for a fraction of the total residence time within the drying chamber. For example, an HSPC can be present in a high heat zone for less than about 50% of the residence time, less than about 40% of the residence time, less than about 30% of the residence time, less than about 20% of the residence time, less than about 10% of the residence time, less than about 8% of the residence time, less than about 5% of the residence time, less than about 4% of the residence time, less than about 3% of the residence time, less than about 2% of the residence time, or less than about 1% of the residence time.

Drying methods can further comprise subsequent low-temperature, long-duration (LTLD) heating of an HSPC after PCSD. For example, heating of egg white powders at 75-80° C. for 10-15 days is widely used in industry to offset functional property losses resulting from traditional spray-drying process. In some embodiments, LTLD heat treatment comprises heating a composition to a temperature below a denaturation temperature. In the same and other embodiments, LTLD heat treatment further comprises heating a composition for longer than 1 hour, longer than 6 hours, longer than 12 hours, longer than 24 hours, longer than 5 days, or longer than 10 days.

Drying methods can additionally or alternatively comprise pasteurization. Pasteurization can include heating a dried HSPC for an amount of time to a minimum temperature. Minimum times and temperatures can be determined based on government regulations, for example. Pasteurization allows an HSPC to be used safely in food and beverage products without prior heating, cooking, or baking.

Drying efficiency of the methods described herein can be measured using the latent heat of evaporation of water compared to the actual energy consumption of a drying technique per unit of dried moisture. Drying efficiency can be measured in total, or for discrete drying steps. For example, the efficiency of a drying method which includes PCSD or SD and subsequent LTLD drying can describe the combined drying efficiency for the entire process, or individually for the PCSD phase and the subsequent LTLD drying phase. Similarly, efficiency can be provided for a percent moisture reduction. For example, efficiency can described the drying efficiency of one or more drying stages that bring an HSPC from 80% water to 10% water. PCSD methods are desirable as they provide high drying efficiencies in drying HSPCs to low moisture contents without compromising the beneficial attributes of the HSPCs. In some embodiments, PCSD methods are at least 25% more efficient than conventional spray drying. PCSD methods can be up to 50% more efficient than conventional spray drying.

In particular, PCSD techniques may be applied to drying heat-sensitive materials, such as HSPC, and biomaterials to achieve both high product quality and process energy efficiency as compared to heat-sensitive materials dried by conventional techniques such as spray drying. Drying can include removing moisture, or the presence of liquids. In some embodiments moisture includes water.

In many embodiments, a pre-dried HSPC can comprise one or more of water, one or more protein, one or more carbohydrates, one or more fats, and one or more oils. A dried HSPC can comprise less than about 30% water, less than about 20% water, less than about 10% water, less than about 8% water, less than about 5% water, less than about 1% water. Dried HSPCs provided herein comprise low amounts of ash, particularly as compared to HSPCs dried by traditional spray drying. A dried HSPC can comprise less than about 10% ash, less than about 7% ash, less than about 5% ash, less than about 4% ash, less than about 3% ash, less than about 2% ash, or less than about 1% ash. Dried HSPCs provided herein further have low protein denaturation, particularly as compared to HSPCs dried by commercially viable methods, in particular traditional spray drying. The protein fraction of a dried HSPC can have a percent protein denaturation less than about 10%, less than about 8%, less than about 6%, less than about 4%, less than about 2%, less than about 1.5%, less than about 1%, or less than about 0.5%.

PCSD techniques can be applied to drying HSPCs to yield compositions with superior color characteristics. Because of the short residence times of a material in PCSD, lower dryer outlet temperatures, and reduced oxygen concentration in the flue gas as compared to traditional spray drying, HSPC materials dried by PCSD exhibit superior color quality. A color change observed in an HSPC after drying can indicate heat damage, oxidation, and/or protein denaturation during the drying process. Similarly, the color of a dried HSPC can be used to compare physical properties with another dried HSPC or to determine if a particular dried HSPC meets a physical specification, such as percent protein denaturation.

In some embodiments, color quality of a dried HSPC can be measured, in part, by whiteness, or a reduced diminishment of whiteness. In other embodiments, color quality of a dried HSPC can be measured, in part, by a reduced darkening of a dried HSPC. Color quality measurements can be made in comparison to a reference material, such as a commercial product or a material dried by traditional spray drying. Color quality measurements can be made using the CIE 1976 L/a/b/ colour space system, wherein L represents color lightness (black is defined as L=0, and diffuse white is defined as L=100), "a" represents the green-magenta scale (negative a values denote green, and positive a values denote magenta, and "b" represents a yellow-blue scale (negative b values denote blue, and positive b values denote yellow).

For many commercial products, for example dried egg whites, a desirable whiter color is achieved by adding additives and/or colorants such as $TiO_2$. The PCSD drying process described herein is capable of providing whiter products, such as dried egg whites and powdered milk, which advantageously reduce or eliminate the need for additives. Accordingly, an HSPC dried by PCSD can comprise little to no additives while still having a desirable white color.

Embodiments herein provide for one or more of smaller particle size and more consistent particle size of a HSPC dried by PCSD. A smaller particle diameter creates a higher surface area to volume ratio of a composition, which increases contact surface with the drying gas and subsequently drying rate and efficiency. Additionally, embodiments herein provide for dried HSPCs which have a hollow morphology. Both smaller particle size and hollow morphology are desirable qualities, which, in some instances, allow for easier and/or more rapid reconstitution of the dried HSPC. Reconstitution can include combining an HSPC with a liquid, such as water.

Consistent particle size can be advantageous for packaging and product aesthetic purposes. Further, larger and/or irregular particle sizes can indicate one or more of a higher degree of protein agglomeration caused by denaturation, and inconsistent atomization within a dryer. HSPCs dried by PCSDs have higher particle size consistency as compared to HSPCs dried by traditional spray drying methods. This is because PCSD utilize low pressure feed conveyers to meter feed into a drying chamber, rather than nozzles or rotary disk atomizers which wear out over time and cause inconsistent feed conveying and atomization. Inconsistent feed conveying and atomization further leads to less control over the temperature differential between the drying gas and feed, and, in some cases, a higher degree of protein denaturation. In some embodiments, a HSPC dried by PCSD can have a relative span factor (RSF) of less than about 3.4, less than about 3.2, less than about 3.0, less than about 2.8, or less than about 2.6. (RSF) indicates uniformity of size distribution and is calculated according to the equation RSF=(D90−D10)/D50, where D10, D50, D90 are particle sizes for 10%, 50% and 90% cumulative mass respectively. An RSF closer to 1 indicates a more uniform size distribution. In other embodiments, a HSPC dried by PCSD can have a mean particle diameter of about 5 μm to about 100 μm, about 10 μm to about 80 μm, about 20 μm to about 60 μm, about 30 μm to about 40 μm, or about 35 μm.

Conventional drying processes such as traditional spray drying can diminish useful physical properties of HSPC. In particular, the foaming ability, foam stability, gel hardness, and gel springiness of an HSPC can be diminished.

The compositions and methods herein provide dried HSPCs having superior foaming abilities as compared to HSPCs dried by conventional methods. Further, HSPCs can have adequate or superior foaming ability, foam stability, gel hardness, and gel springiness without the addition of additives such as soaps. In some embodiments dried HSPCs can further comprise additional additives to enhance physical properties, such as foaming ability, foam stability, gel hardness, and gel springiness. In some embodiments, dried HSPCs can further comprise sodium lauryl sulfate and/or soaps. In many embodiments, additives are chosen such that they are suitable for consumption by humans and/or animals.

The compositions and methods herein also provide dried HSPCs having superior gelling abilities as compared to HSPCs dried by conventional methods. Dried HSPCs provided herein can further comprise additional additives which may enhance foaming ability.

Example One: Egg White Drying by PCSD Techniques

Figure 3B:
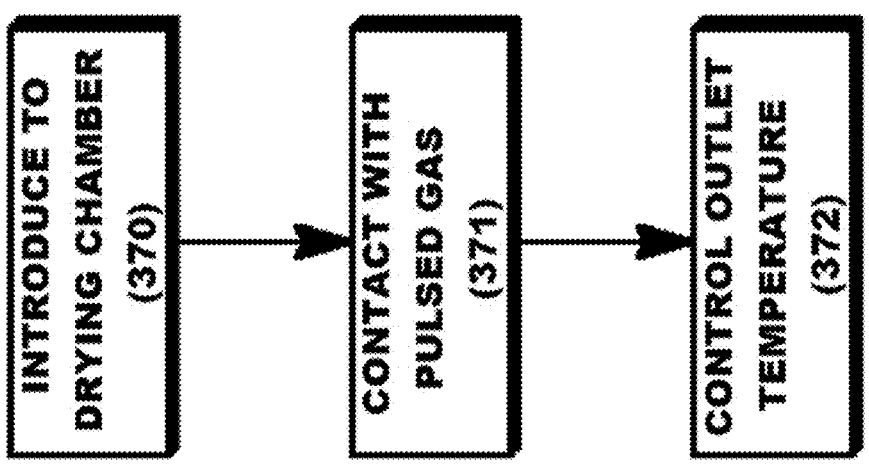

Production of the egg white powder was conducted on a PCSD pilot installation as shown in FIG. 3. The process parameters were monitored and their values were used to calculate the energy efficiency of the PCSD drying process. The physical, chemical and functional properties of PCSD dried egg white powders compared with the properties of a commercial product obtained by traditional spray drying, and an experimental control dried by low heat hot air drying.

The pulse combustion spray drying pilot testing installation was developed by Pulse Holdings LLC, USA, and consisted of a pulse combustor, a tall-form drying chamber, a cyclone and a bag house. The installation was designed to have a heat release of 29.3 kW and evaporative capacity of 40 kg water/hour. The pulse combustor operated on the gaseous fuel-propane and the tall-form drying chamber had a diameter of 1.3 m, height of 3 m and volume of 4 m$^3$. A-low pressure, open pipe feed system was used supply the liquid.

The raw material, GREAT VALUE™ 100% liquid egg white, was purchased from local Wal-Mart store in Payson, Ariz., USA. The material comprised 10.87% protein, almost 0.0% total fat, 2.17% total carbohydrate, 86.96% water, according to the product label. Feed solid was therefore 13.04%. 25 kg of liquid egg white was purchased and mixed in the feed tank. At the beginning of the experiment, the PC dryer was ignited and then warmed up in the first 30 minutes without liquid feed. During warming up, the PC dryer setup was being adjusted to an optimum drying condition for the liquid egg whites: the heat release was set to be 83.000 BTU/hr (24.32 kW) and taking the heat value of propane as 2200 BTU/m$^3$ (2321 kJ/m$^3$), the fuel flow rate was calculated to be 0.63 m$^3$/min. The combustion gas temperature at the atomizer was adjusted to be 326.6° C.

After the warming up of the PC dryer, liquid egg white was fed into the dryer at a speed of 0.6 kg/min. The egg whites were atomized and dried simultaneously by the high velocity, oscillating combustion gas exiting the pulse combustor and entering the drying chamber. The gas temperature in the chamber bottom was measured to be 76.6° C. and ambient air temperature was 25° C. The whole egg white drying process lasted about 28 minutes. The dried egg white powders were collected from the cyclone, baghouse, and the blow-down of the wall deposit on the drying chamber. All the powders were mixed together and stored in a tightly closed bag for sequent properties testing. Table 1 summarizes the operation data obtained for the PCSD process of egg white:

TABLE 1

Operation data for the PC spray drying process of egg white:

| | |
|---|---|
| Feed rate of the liquid egg white | 0.6 kg/min |
| Initial moisture content | 86.96% |
| Heat release of PC combustor | 24.32 kw |
| Gas temperature at the feeding point | 326.6° C. |
| Gas temperature at the drying chamber outlet | 76.6° C. |
| Ambient air temperature | 25.0° C. |
| Running time | 28 min |
| Dry solids fed during run | 2.19 kg |
| Powders from cyclone | 1.32 kg (60.28%) |
| Powders from chamber wall blowdown | 0.29 kg (13.24%) |
| Powders from chamber wall brushdown | — |
| Powder from baghouse | — |
| Total yield | 73.52% |
| Final moisture content of powders | 8.11% |
| Water evaporation rate | 33.62 kg water/hr |
| Volume evaporation rate | 8.41 kg water/hr · m$^3$ |
| Energy consumption | 2604 kJ/kg water evaporated |

From Table 1, it can been seen that when the PC dryer operated in a heat load of 24.32 kw (80% of its design capability), the dryer can reduce the moisture content of the egg white from its initial 86.96% to the final 8.11% in a feeding rate of 0.6 kg/min. In this condition, the evaporation rate of the PC spray dryer was calculated to be 33.62 kg water/hr (84% of its designed capability) and the produce capability was 36 kg liquid egg white/hr. The energy consumption was calculated to be 2604 kJ/kg water evaporated, which is slightly higher than the water evaporation latent heat of 2258 kJ/kg. Compared with the traditional spray dryers with energy consumptions of 4500-11500 kJ/kg, the PCSD dyer has a very low energy consumption and high energy efficiency. The drying gas temperature in the PC dryer reached 326.6° C. compared to traditional spray dryers which use a drying gas temperature of 110-150° C. for heat sensitive food materials. Using the latent heat of evaporation as a benchmark for efficiency, the PCSD operated with an 86.7% efficiency, as compared to traditional spray dryers which operate with a 19.6% to 50.2% efficiency.

Table 1 shows that 60.28% dry solid feed was collected from the cyclone and 13.24% dry solid was collected from the drying chamber wall blowdown at the end of the pilot test. The total yield of the egg white dry solid feed is about 73.52%. It was observed that the egg white powders deposited on the chamber wall can be easily blown down using the compressed air. The fact means that the wall deposit of egg white powders was minor in the PC spray dryer. The about 26.48% dry solid feed was lost largely due to the multi-purpose cyclone of the pilot dryer which was not optimized for egg white powder collection.

The measurement of product colors were repeated four times and three samples were analyzed for other product properties. The data were processed to obtain the maximum, minimum, mean value, standard deviation, and range as shown in Tables 2-4. The physical, chemical and functional properties of the egg white powders obtained by the PCSD technique were measured and compared with the ones of a commercial egg white powder product obtained using traditional SD technique from Kangde Company, Nantong City, China.

The major components of the initial egg white include water, protein, fat and carbohydrate. The water content, $M_w$, was measured using the traditional drying oven method. The mass fraction of total protein, $M_p$, was measured using the Kjeldahl determination method according to the Chinese national standard (GB/T5009.5-2010). The mass fraction of the total fat, Mf, was measured using Soxhlet extraction method according to the Chinese national standard (GB/T 1477.2-2008). The concentration of carbohydrate, $M_c$, was calculated by the equation (1):

$$M_c = 1 - (M_w + M_p + M_f) \qquad (1)$$

The initial liquid egg white comprised 10.87% protein, almost 0.0% total fat, 2.17% total carbohydrate, 86.96% water. The PCSD powders comprised 8.11±0.13% water, 73.97±1.45% protein, 0.18±0.03% total fat, 13.17% total carbohydrate and 4.57% ash.

The color of the PCSD and SD egg white powders was measured using the DC-P3 colorimeter (Beijing Xingguang Color Measurement Instrument Co., Ltd, Beijing, China). The color was measured using an absolute measuring mode following the manufacturer's instruction and calculated automatically using the CIE 1976 L/a/b/ colour space system (International Commission on Illumination, 2008). Table 2 shows color parameters for the PCSD dried egg white, and the Kangde™ spray dried egg white:

TABLE 2

Statistics of the Color Parameters for PCSD and Kangde™ Spray Dried Egg White:

| Items | Maximum | minimum | Mean | Standard Deviation | Range |
|---|---|---|---|---|---|
| PCSD powders | | | | | |
| L | 79.90 | 79.86 | 79.88 | 0.02 | 0.04 |
| a | −4.98 | −4.94 | −4.96 | 0.02 | 0.04 |
| b | 8.62 | 8.60 | 8.61 | 0.01 | 0.02 |
| SD powders | | | | | |
| L | 77.92 | 77.91 | 77.91 | 0.01 | 0.01 |
| a | −6.23 | −6.20 | −6.21 | 0.01 | 0.03 |
| b | 10.42 | 10.31 | 10.35 | 0.05 | 0.11 |

Figure 4A:
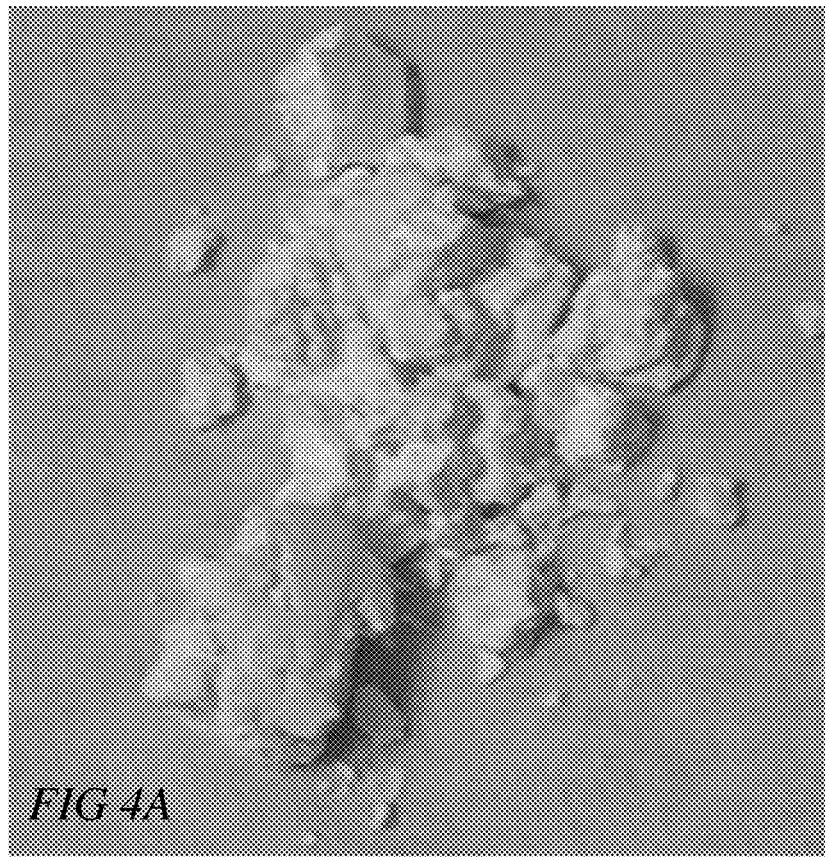
Figure 4B:
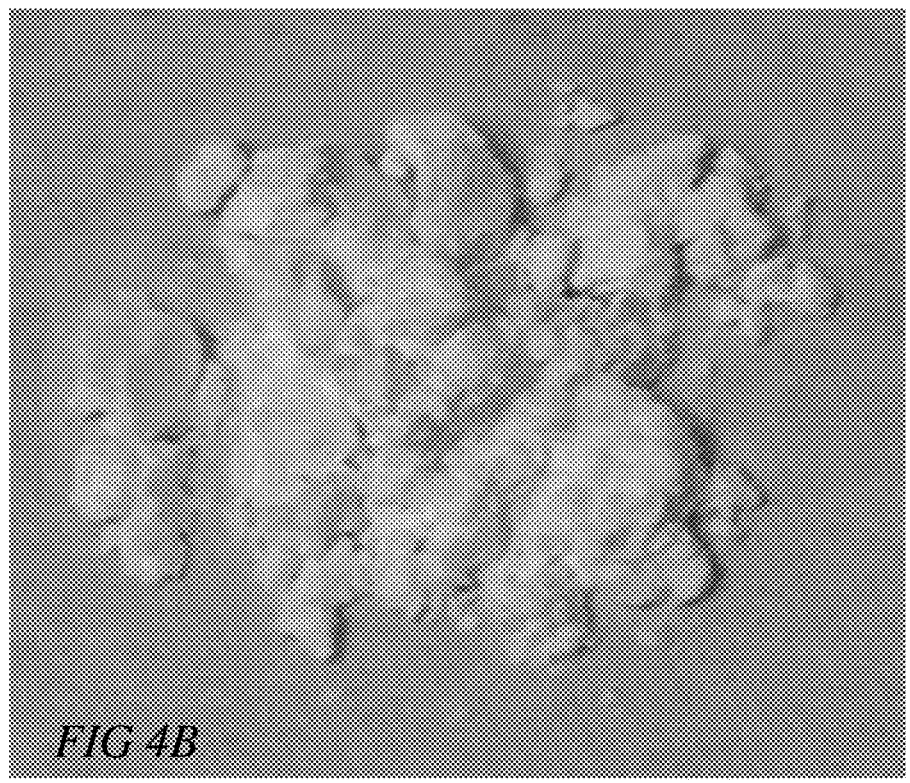

As shown Table 2, the PCSD dried egg white powders have a smaller mean particle diameter than the traditional SD dried egg white powders. FIGS. 4A and 4B show the pulse combustion spray dried and traditional spray dried egg white powders, respectively. The PCSD powders have a white color while the SD powders have a pale yellow color. When measured using the DC-P3 colorimeter, the PCSD powders had an L value of 79.87, an a value of −4.96 and a b value of 8.60. While the SD powders had an L value of 77.91, an A value of −6.21 and a B value of 10.33. The whiter color of the PCSD powders indicates a lower degree of protein denaturation as compared to the SD powders, among other things.

Figure 5:
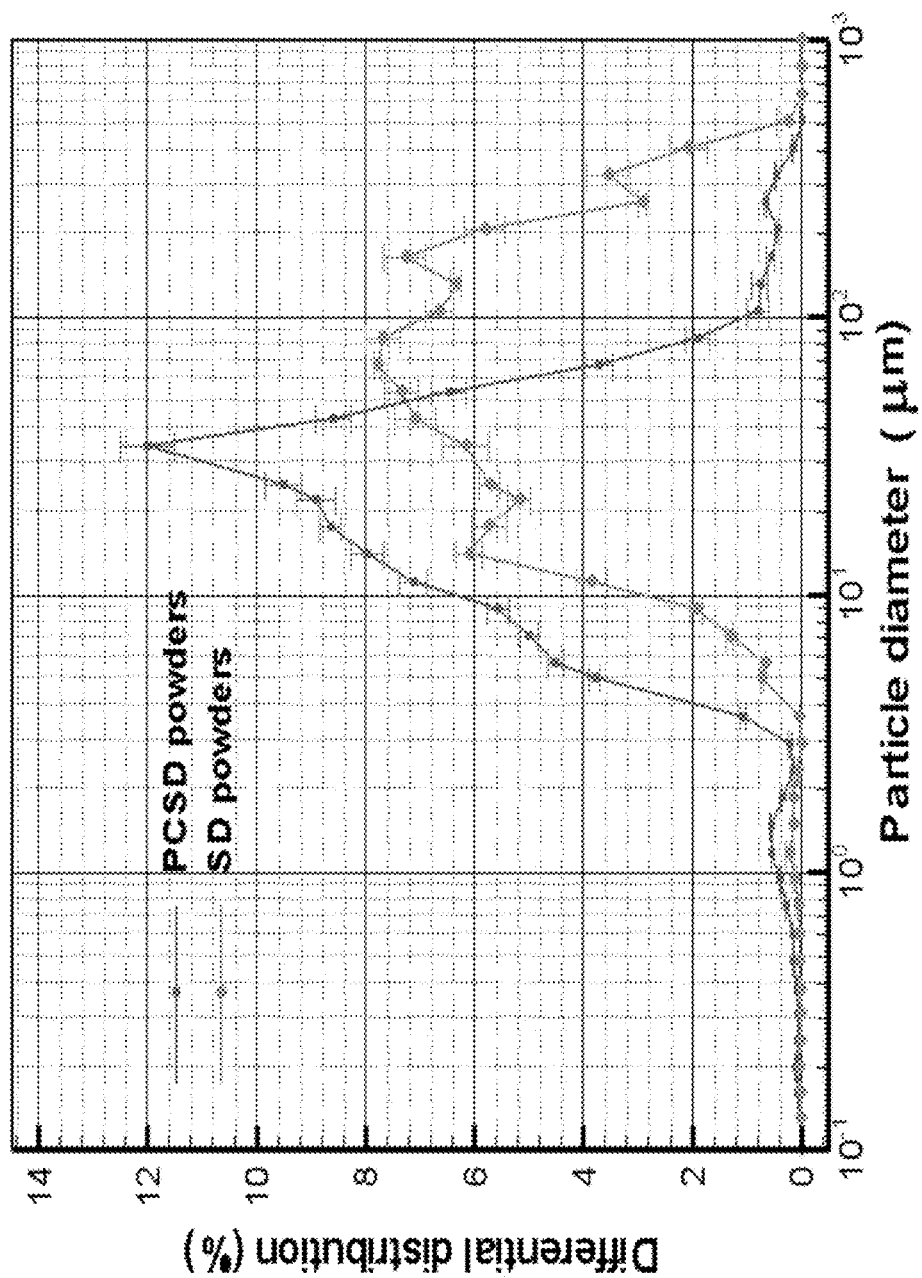

The particle size distribution of PCD egg white powders were measured using the laser diffraction method on a LS-C(III) Laser Particle Size Analyzer (OMEC, Zhouhai, China) with a size range of 0.1-1000 μm. Each sample was measured three times and the size distribution curves were plotted in FIG. 5 in comparison with spray dried egg whites. The differential distribution in FIG. 5 is the percentage of particles from the total are within a specified size range. The cumulative distribution is the sum of the differential distribution. The distribution width expressed as the relative span factor (RSF) was calculated according to the equation RSF= (D90−D10)/D50, where D10, 50, D90 were particle sizes for 10%, 50% and 90% cumulative mass respectively.

The D50 diameter of the PCSD powders was 20.15 μm while the SD powders had a D50 diameter of 54.74 μm. The RSF parameters, which are used to express the particle size uniformity, are 2.71 for the PCSD powders and 3.42 for the SD powders respectively, showing the PCSD powders had a more consistent particle size. As shown in FIG. 5, the PCSD dried egg white powders have a smaller mean particle diameter and tighter size distribution than the traditional SD dried ones. A smaller particle diameter creates a larger surface area to volume ratio of the egg white that increases drying rate.

Morphologies of the PCSD and SD egg white powders were analyzed using the SU-1510 Scanning Electron Microscopy (Hitachi, Japan). Samples were prepared on the aluminum SEM stubs. The mounted powders were sputter-coated with gold-palladium, achieving a coating thickness of approximately 15 nm. The electron micrographs were produced by the SEM in secondary electron mode with an operating voltage of 5 keV. A range of 50 to 1500 magnification was used in the images.

Figure 6A:
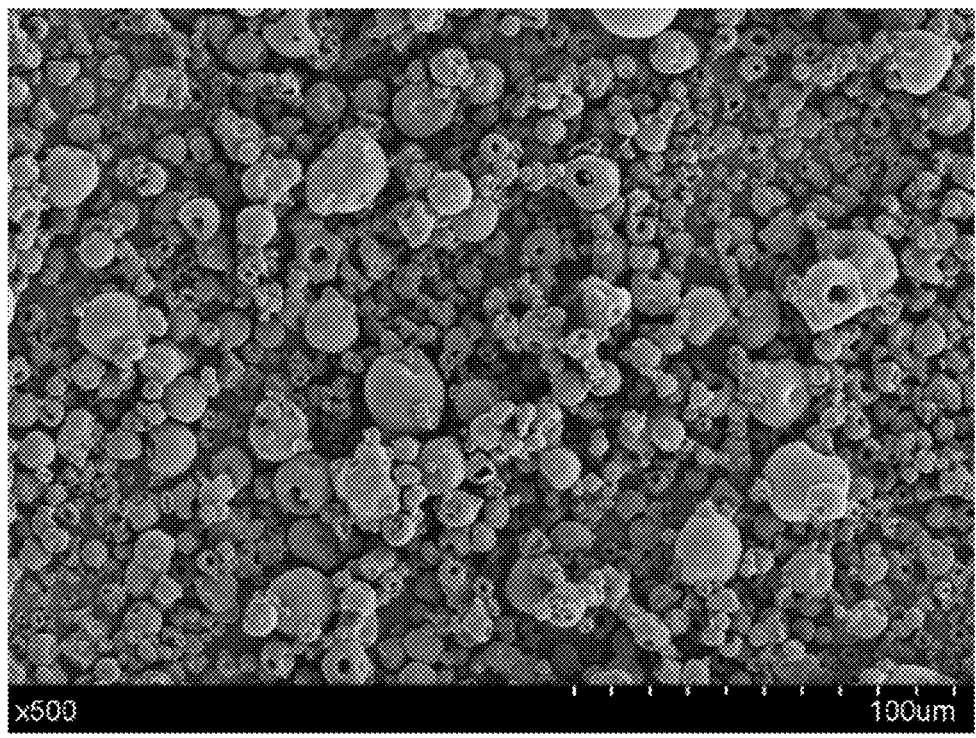
Figure 6B:
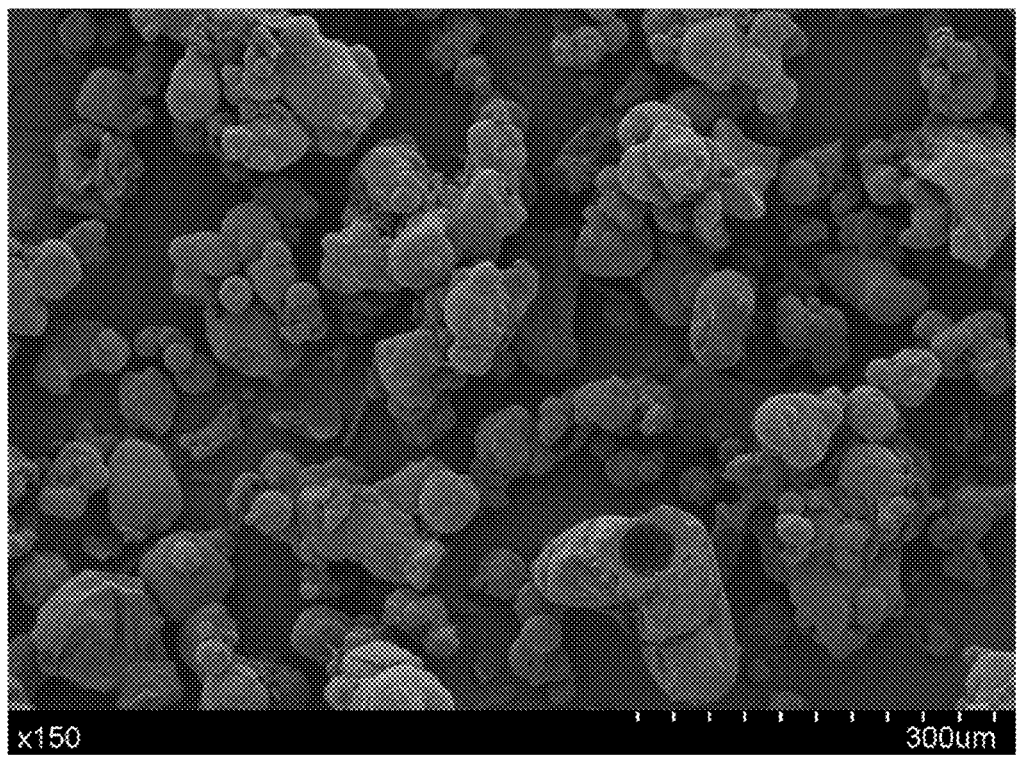

FIGS. 6A and 6B show the SEM images of PCSD and SD egg white powders, respectively. From FIGS. 6A and 6B, it can be seen that the PCSD powders had a superior particle surface characteristics. The SEM images showed that most PCSD powders were single and disperse, with a sphere shape and smooth surface. By contrast, the SD powders easily aggregated to form bigger particles that had various shapes and coarse surface. Also, the PCSD powders had a hollow structure while SD powders had a dense solid structure. This hollow structure may be caused by fast drying rate and short residence time of the egg white in the PC dryer, which does not allow droplets to shrink fully. In contrast, the moderate drying rate and low temperatures of traditional spray drying allow egg white droplets to fully shrink and create a denser, solid structure.

Figure 7:
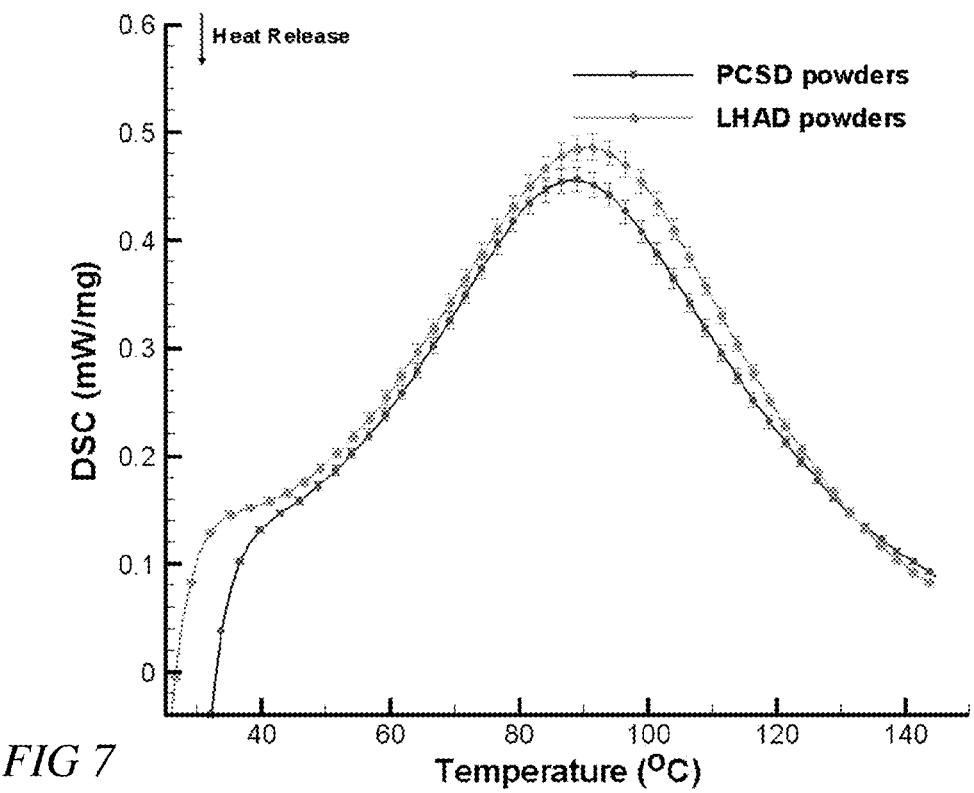

The protein denaturation level of the egg white powders was determined using a differential scanning calorimetry (DSC) method on a DSC204 FI differential scanning calorimeter (Netzsch, German). Samples of 8.7 mg egg white powders were loaded in hermetically sealed aluminum pans using a pipette. An empty pan was used as reference. Samples were first equilibrated at 30° C. for 5 minutes and then, the temperature was raised to 150° C. at a speed of 5° C./min. FIG. 7 shows the DSC curves for the PCSD powders and LHAD sample. Total denaturation enthalpies were calculated from the DSC curves, and the degree of denaturation in percentage relative to the low temperature hot air dried (LHAD) sample was calculated. The LHAD sample was obtained by drying the initial liquid egg white to a dry solid with final moisture of 8% in a hot air convective drying oven using a drying air temperature of 40° C. The low drying heat of the LHAD method as compared to the egg white protein denaturation temperature (89° C.) allows a 0% protein denaturation to be assumed.

From FIG. 7, it can be seen that the egg white protein denaturation temperature was about 89° C. The protein denaturation degree of the PCSD powder relative to the LHAD sample was 98.4%, indicating that little protein denaturation occurs in the PC drying process (e.g., 1.6% protein denaturation). This is supported by Table 1, which shows a drying chamber gas outlet temperature (76.6° C.) below the egg denaturing temperature.

Foaming ability (FA) and foam stability (FS) of egg white powders were measured by mixing dried egg white powders with distilled water to form a 40% mass fraction egg white solution. Next, the pH of a 25 ml egg white solution was adjusted to 8. The solution was then homogenized using an emulsification machine at the speed 14000 min$^{-1}$ for 2 minutes and a post-emulsification volume, $V_0$, was measured. After standing for 30 minutes, the new volume, $V_{30}$, was measured. The FA and FS were calculated using the following equations (2) and (3) respectively.

$$FA = \frac{V_0 - V_{int}}{V_{int}} \times 100\% \quad (2)$$

$$FS = \frac{V_{30} - V_{int}}{V_0 - V_{int}} \times 100\% \quad (3)$$

where $V_{int}$ is the initial volume of the solution, 25 ml. Table 3 shows the measured foaming properties of the PCSD, Kangde™ SD and LHAD egg white powders:

TABLE 3

Statistics of the foaming properties for PCSD, Kangde™ SD egg white powders and LHAD sample:

| Items | Maximum | minimum | Mean | Standard Deviation | Range |
|---|---|---|---|---|---|
| Foaming ability (%) | | | | | |
| PCSD | 28.0 | 24.8 | 26.3 | 1.3 | 3.2 |
| SD | 38.0 | 37.2 | 37.7 | 0.4 | 0.8 |
| LHAD | 38.0 | 32.0 | 36.0 | 2.8 | 6 |
| Foam stability (%) | | | | | |
| PCSD | 96.9 | 88.7 | 92.8 | 3.4 | 8.2 |
| SD | 96.8 | 95.8 | 96.5 | 0.5 | 1 |
| LHAD | 84.2 | 73.7 | 79.7 | 4.4 | 10.5 |

In Table 3, it can be seen that the Kangde™ SD powders had the best mean foaming ability of 37.73% and foam stability of 96.46%, which is likely attributed to soap additives not present in the PCSD sample. The LHAD sample had a similar mean foaming ability with the SD powders, but its mean foam stability was low (79.56%) as compared to the PCSD sample (92.8%). The additive-free PCSD powders exhibited comparable foam stability to the SD powders.

Gelling properties of egg white powders were measured by mixing dried egg white powders with distilled water to form a 40% mass fraction egg white solution. Next, the pH of a 25 ml egg white solution was adjusted to 8. Egg white gels were prepared by heating 300 mL of the egg white solution with a 19% protein concentration in plastic tubes in a water bath at 80° C. for 1 hour, and subsequently cooled at room temperature for at least 4 hours. After removing the tubes, cylindrical samples (3 cm diameter, 2 cm high) were cut using two parallel metal wires. The texture of the gel samples was measured using a TA-XT2 texture analyzer (Stable Micro System Ltd, UK). A 20 mm diameter plate probe was used a texture profile analysis (TPA) in a double compression test to penetrate to 50% depth at a penetration speed of 2 mm/s. The gel hardness and springiness were calculated from the TPA system. Table 4 shows the measured gelling properties of the PCSD, Kangde™ spray dried, and LHAD egg white powders:

TABLE 4

Statistics of the gelling properties for PCSD, Kangde™ SD egg white powders and LHAD sample:

| Items | Maximum | minimum | Mean | Standard Deviation | Range |
|---|---|---|---|---|---|
| Hardness (g) | | | | | |
| PCSD | 1082.3 | 900.0 | 957.6 | 88.3 | 182.3 |
| SD | 520.7 | 450.6 | 486.5 | 28.7 | 70.1 |
| LHAD | 1120.4 | 984.6 | 1080.4 | 68.1 | 135.8 |
| Springiness (%) | | | | | |
| PCSD | 96.1 | 91.5 | 94.1 | 1.9 | 4.6 |
| SD | 90.3 | 83.7 | 85.1 | 3.8 | 6.6 |
| LHAD | 92.4 | 82.8 | 88.3 | 4.1 | 9.6 |

In Table 4, the LHAD sample has the best gelling properties with a hardness of 1100 g. Compared with the LHAD sample, there is a slight reduction of 11.3% for the PCSD powder but a drastic reduction of 55% in hardness for the Kangde™ SD powders. From Table 4, it can be concluded that egg whites powders dried by PCSD techniques have superior gelling properties than egg white powders dried by traditional SD operations.

Example Two: Differential Scanning Calorimetry (DSC) Analysis of Various Egg White Drying Techniques Egg whites were dried using hot air drying, vacuum freeze drying, traditional spray drying (SD) and PCSD, and heat release was measured using DSC. DSC was performed using an SDT-Q600 Synchronism Thermal Analyzer (TA instrument, USA). Measurement conditions included a temperature range of 20-150° C., a temperature increase rate of 5° C./min, and sample weights of 15-20 g. Hot air drying was conducted by drying egg whites in a hot air drying oven at 45° C. Vacuum freeze drying was conducted by freezing egg whites to −80° C., and subsequently drying in a vacuum freeze dryer. Traditional SD and PC spray drying of egg whites was conducted using respective methods as described above.

Figure 8:
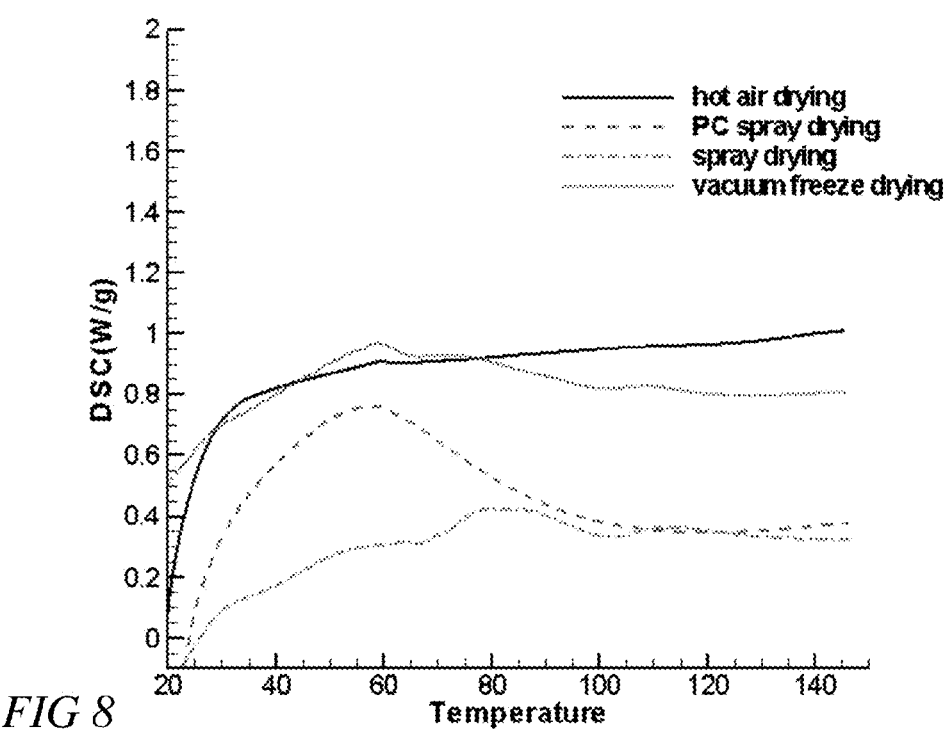

DSC results are shown in FIG. 8. While hot air drying and vacuum freeze drying methods offer the highest heat release at lower temperatures, these methods are not commercially viable. Hot air drying yields high quality dried products, but is too inefficient to warrant use outside of a laboratory environment. Freeze drying is similarly slow, but also expensive and cumbersome. Among the two commercially viable drying methods, it can be seen that PC spray drying methods have significantly higher heat release than traditional SD methods at lower temperatures (i.e., below about 80° C.). High heat release below protein denaturation temperatures allows for efficient drying without degradation to a dried sample, such as a HSPC.

What is claimed is:

1. A method for producing a dried protein-containing composition, the method comprising:
   introducing a heat-sensitive protein composition into a drying chamber, wherein the heat-sensitive protein composition comprises water and one or more proteins;
   drying the heat-sensitive protein composition by contacting the heat-sensitive protein composition with a pulsed gas stream of a pulse combustion dryer;
   controlling the drying chamber outlet temperature such that the temperature of the heat-sensitive protein composition exceeds but does not substantially exceed a denaturation temperature of one or more proteins in the heat-sensitive protein composition; and
   recovering a dried protein-containing composition.

2. The method of claim 1, wherein controlling the drying chamber outlet temperature such that the temperature of the heat-sensitive protein composition exceeds but does not substantially exceed the denaturation temperature of one or more proteins in the heat-sensitive protein composition comprises manipulating one or more of the pulsed gas stream temperature, a residence time of the heat-sensitive protein composition within the drying chamber, pulsed gas stream pulse frequency, pulsed gas stream exit temperature, or feed flow rate.

3. The method of claim 1, wherein heat-sensitive protein composition is introduced in a portion of the pulsed gas stream having a temperature that exceeds the denaturation temperature of one or more proteins in the heat-sensitive protein composition by at least 50° C.

4. The method of claim 1, wherein the residence time of the heat-sensitive protein composition within the drying chamber is less than 5 seconds.

5. The method of claim 1, wherein the heat sensitive protein composition is exposed to a peak temperature of the pulsed gas stream in a high-heat zone of the drying chamber for less than about 50% of the residence time of the heat-sensitive protein composition within the drying chamber.

6. The method of claim 1, wherein the dried protein-containing composition comprises less than 10% water.

7. The method of claim 1, wherein a drying efficiency based on percent moisture reduction is at least 50% efficient.

8. The method of claim 1, further comprising subsequent low-temperature, long-duration heat treatment, wherein the heat treatment includes heating a heat-sensitive protein composition to a temperature below a denaturation temperature for at least 1 hour.

9. The method of claim 1, further comprising pulsing the gas stream at a frequency of pulses between 50 Hertz and 200 Hertz.

10. The method of claim 1, further comprising cooling a feed introduction pipe to prevent the heat-sensitive protein composition from substantially heating before contacting the pulsed gas stream.

11. The method of claim 1, wherein recovering the dried protein-containing composition includes passing the dried protein-containing composition through a cyclone separator.

12. The method of claim 1, wherein a heat-sensitive protein composition comprises one or more of egg whites, milk, gelatins, casein, whey, soy, or gluten.

13. The method of claim 1, wherein a protein fraction of the dried protein-containing composition has a percent protein denaturation less than 10%.

* * * * *